United States Patent [19]
Perkins

[11] Patent Number: 6,126,629
[45] Date of Patent: Oct. 3, 2000

[54] MULTIPLE PORT PHACO NEEDLE

[75] Inventor: James Taylor Perkins, St. Charles, Mo.

[73] Assignee: Bausch & Lomb Surgical, Inc., Claremont, Calif.

[21] Appl. No.: 09/215,893

[22] Filed: Dec. 18, 1998

Related U.S. Application Data

[60] Provisional application No. 60/068,010, Dec. 18, 1997.

[51] Int. Cl.[7] .................................................. A61B 17/20
[52] U.S. Cl. .............................................. 604/22; 604/294
[58] Field of Search ................................. 604/22, 35, 39, 604/43–44, 21, 46, 239, 272–274, 264, 268, 294; 606/107, 161, 166, 171, 223

[56] References Cited

U.S. PATENT DOCUMENTS

| | | |
|---|---|---|
| D. 357,313 | 4/1995 | Wortrich . |
| 4,531,934 | 7/1985 | Kossovsky et al. . |
| 4,643,717 | 2/1987 | Cook et al. . |
| 4,689,040 | 8/1987 | Thompson . |
| 4,816,018 | 3/1989 | Parisi . |
| 4,869,715 | 9/1989 | Sherburne . |
| 4,959,049 | 9/1990 | Smirmaul . |
| 5,084,009 | 1/1992 | Mackool ..................................... 604/22 |
| 5,151,099 | 9/1992 | Young et al. ............................... 606/27 |
| 5,154,694 | 10/1992 | Kelman . |
| 5,213,569 | 5/1993 | Davis . |
| 5,417,654 | 5/1995 | Kelman . |
| 5,451,229 | 9/1995 | Geuder et al. . |
| 5,676,649 | 10/1997 | Boukhny et al. . |
| 5,743,871 | 4/1998 | Strukel et al. ............................. 604/35 |
| 5,746,713 | 5/1998 | Hood et al. . |
| 5,788,679 | 8/1998 | Gravlee, Jr. . |
| 5,836,959 | 11/1998 | Seibel et al. . |

FOREIGN PATENT DOCUMENTS

| | | |
|---|---|---|
| WO94/08518 | 4/1994 | WIPO . |
| WO 98/14148 | 4/1998 | WIPO . |

*Primary Examiner*—Wynn Wood Coggins
*Assistant Examiner*—Manuel Mendez
*Attorney, Agent, or Firm*—Grant D. Kang

[57] ABSTRACT

The present invention provides a phacoemulsification needle having an improved distal tip. The distal tip is provided with a generally rounded closed distal end having a plurality of longitudinally extending ports provided therein communicating between the interior lumen of the needle and exteriorly of the needle. The outer surface of the distal end is rounded to provide a smooth surface so as to not cut or snag an eye tissue. Two embodiments of the phacoemulsification needles are shown having five and nine ports therethrough, respectively.

4 Claims, 2 Drawing Sheets

MULTIPLE PORT PHACO NEEDLE

This application is a provision of Ser. No. 60/068,010 filed Dec. 18, 1997.

TECHNICAL FIELD OF THE INVENTION

The present invention relates to surgical instruments, and, more particularly, to an improved tip for a phacoemulsification needle used in opthalmic cataract surgery.

BACKGROUND OF THE INVENTION

A phacoemulsification surgical instrument provides for the breaking apart and the removal of unwanted tissue and material, especially a cataract located in the capsular bag or sac of the eye, by ultrasonically fragmenting the cataract while simultaneously introducing fluid into the eye and withdrawing the fluid and fragmented cataract particles from the eye. A typical phacoemulsification instrument includes a handpiece having an operative needle vibrating in the ultrasonic range. The needle shaft is hollow and is, in turn, surrounded by a tubular sleeve. In operation, the needle shaft, including the surrounding tubular sleeve, is inserted through the anterior chamber of the eye and into the capsular bag. Irrigation fluid is introduced through the hollow sleeve to provide a replacement for fluid withdrawn or lost from the eye chamber during surgery. The needle tip is used to emulsify the cataract. The fluid and fragmented or emulsified cataract are removed from the eye through the hollow needle via a suction source provided through the handpiece.

The capsular bag or sac contains a gel-like lens nucleus which acts to focus light rays entering the eye onto the retina to produce sight. A cataract is a clouting or growth within the gel-like material of the capsular sac. It is desirable to emulsify the lens nucleus in situ because removing the nucleus from its original position and emulsifying the nucleus elsewhere in the eye creates a possibility of damage to other eye tissue, such as damage to the iris and/or corneal endothelium. However, emulsification of the lens nucleus in situ causes additional problems, particularly the danger of rupturing the back of, or the posterior portion, of capsular sac. If the posterior capsular sac surface encounters a sharp instrument, such as a sharpened vibrating needle, or too great a suction is created within the hollow needle, the posterior surface of the capsular bag may be punctured, and once its structural integrity is broken, the capsular bag generally splits and tears.

Danger to the posterior surface of the capsular bag results in the loss of vitreous humor and lens particles and other material falling into the posterior chamber of the eye resulting in undesirable complications, dangers and difficulties in performing cataract surgery and patient recovery. In most cataract operations, once the lens nucleus is removed from the eye, an intraocular lens (IOL) is positioned within the capsular sac. However, if the structural integrity of the capsular sac has been destroyed by piercing or undo vacuum pressures, then the IOL cannot be properly positioned and held within the capsular sac. At this point, a physician's options are limited thus the physician would be required to use an IOL which is affixed within the anterior chamber of the eye. This is often not the optimal placement for an IOL.

A needle has thus arisen for a phacoemulsification needle having a tip which greatly reduces the probability of damaging the integrity of the capsular sac either through piercing or the creation of too much negative pressure.

SUMMARY OF THE INVENTION

Accordingly, an object of the present invention is to provide a new and improved phacoemulsification needle for ultrasonically removing tissue.

Another object of the present invention is to provide a phacoemulsification needle which will not clog during use.

A further object of the present invention is to provide a phacoemulsification needle which provides greater cavitation at its tip then other needles known in the prior art.

A further object of the present invention is to provide a phacoemulsification needle having a tip with rounded edges to prevent eye tissue damage.

A still further object of the present invention is to provide a surgical needle that can be used in either a phacoemulsification surgical mode or an irrigation/aspiration mode without the use of ultrasonic power.

A yet further object of the present invention is to provide a phacoemulsification needle for performing a cataract operation wherein cataract particles are efficiently aspirated from the eye to avoid damage to delicate eye tissue.

In accordance with the present invention, a phacoemulsification needle having an improved distal tip, the needle having a proximal end attached to a phacoemulsification handpiece and a distal end which can be inserted into the eye is provided. The needle includes a central longitudinal axis extending from the proximal end to the distal end with a bore within the needle concentric to the central longitudinal axis thereof, so as to form a lumen therein. The lumen includes needle sidewalls having an inner and outer surface with an opening at the proximal end and a generally rounded closed distal end. The closed distal end has a plurality of longitudinally extending holes provided therein. The outer surface of the distal end is rounded to provide a smooth surface so as to not cut or snag on eye tissue. A first embodiment of the improved phacoemulsification needle includes five (5) generally parallel longitudinally extending holes or ports through the rounded distal end of the needle. A second embodiment of the needle includes nine (9) generally parallel longitudinally extending holes or ports through the rounded distal end of the needle.

BRIEF DESCRIPTION OF THE DRAWINGS

For a more complete understanding of the present invention, and for further advantages thereof, reference is now made to the following description of the preferred embodiments taken in conjunction with the accompanying drawings.

FIG. 1b is an enlarged end view of the prior art needle tip of FIG. 1a;

DESCRIPTION OF THE PREFERRED EMBODIMENT

Figure 1A:
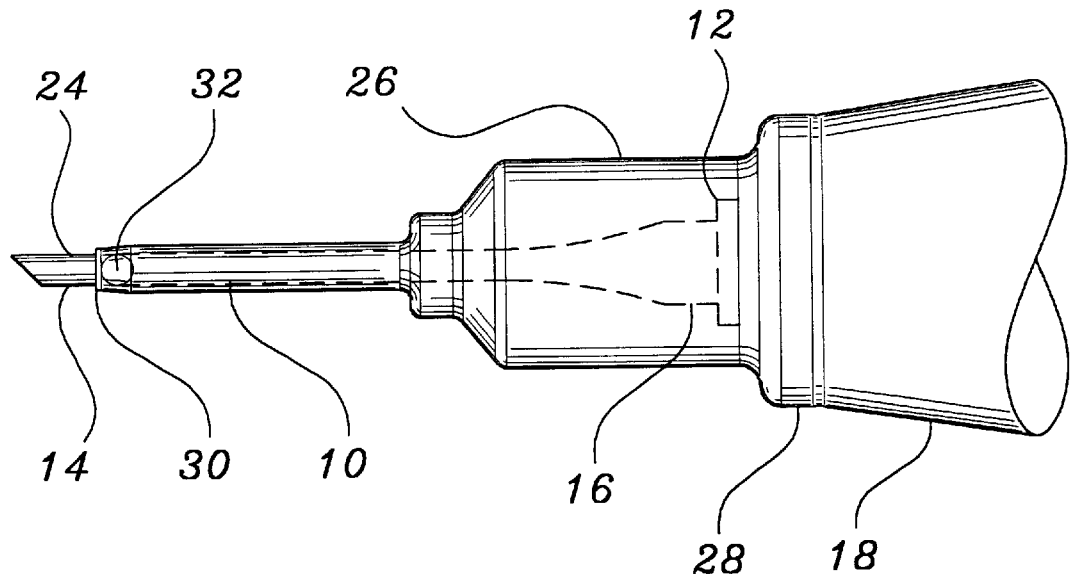
FIG. 1a is a side view of a common prior art phacoemulsification needle and tip attached to a typical ultrasonic handpiece.
Figure 1B:
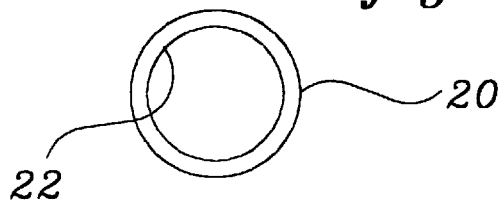

Referring to FIGS. 1a and 1b, a typical phacoemulsification needle, generally referred to by the numeral 10, is illustrated (partially in phantom lines). Phacoemulsification needle 10 includes a proximal hub 12 and a distal end 14. Phacoemulsification needle 10 can be utilized in any ultrasonic system for the break-up and removal of tissue, and is not limited to the break-up and removal of eye lens material, it being understood that such systems, including the present invention, are applicable to many other uses. Phacoemulsification needle 10 includes a threaded proximal portion (not shown) and parallel flats 16 at the proximate hub 12 for attaching the needle 10 to a handpiece 18 of the phacoemulsification system for vibrating the needle 10 in the ultrasonic range. Phacoemulsification needle 10 includes an elongated, thin walled shaft 20 having a lumen 22 and a tip generally identified at 24. A flexible irrigation sheath 26 surrounds most of the needle 10 and has an internally threaded proximal end 28 which is received about the end of handpiece 18. Irrigation sheath 26 has a distal axial opening 30 through which the distal tip 24 extends and further has a pair of diametrically opposed radial holes 32 positioned adjacent the distal axial opening 30 of the sheath. The handpiece 18 is provided with an ultrasonic horn (not shown) for vibrating the needle 10 and a vacuum or aspiration source is connected to lumen 22 to aspirate the emulsified tissue through needle 10. An irrigation source (not shown) is connected to the handpiece 18 for providing an irrigating liquid along the outside of needle 10 and inside irrigation sheath 26 exiting through radial holes 32 to irrigate the surgical site.

Phacoemulsification needle 10 may have an outside diameter of 0.030–0.050 inches and a wall thickness of approximately 0.0035 inches. In cross-section, shaft 20 may be circular as shown in FIGS. 1–5, or slightly elliptical in shape.

Figure 2:
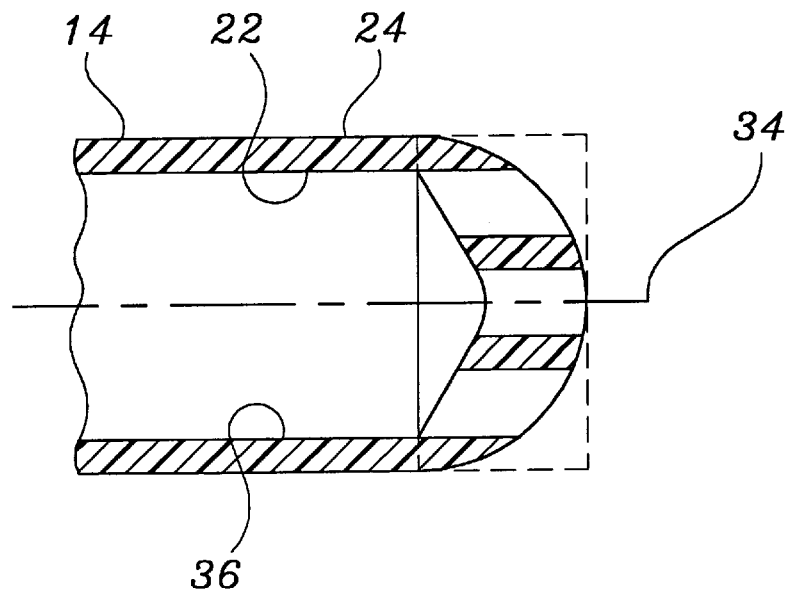
FIG. 2 is an enlarged cross-sectional side view of the phacoemulsification needle tip of the first embodiment of the present invention.
Figure 3:
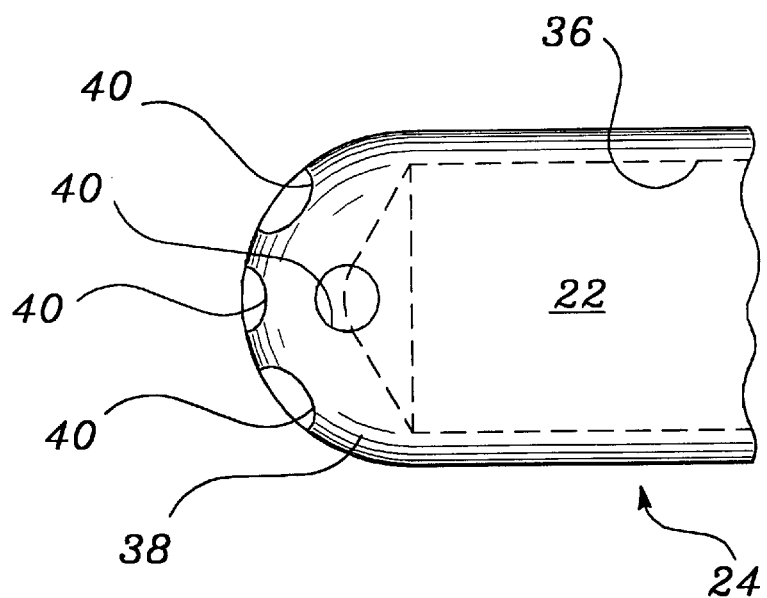
FIG. 3 is an enlarged side view of the phacoemulsification needle tip of the first embodiment of the present invention.
Figure 4:
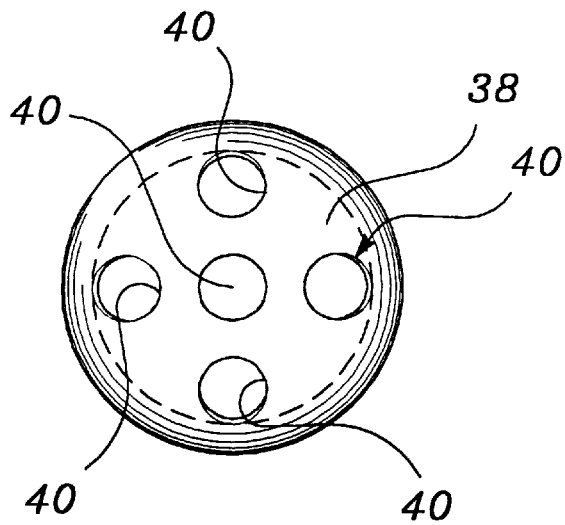
FIG. 4 is an enlarged distal end view of the phacoemulsification needle tip of the first embodiment of the present invention.

Referring now to FIGS. 2–4, a phacoemulsification needle tip 24 is formed on the distal end 14 of needle 10, and is insertable into the eye during surgical procedures. Phacoemulsification needle 10 includes a central longitudinal axis 34 extending from the proximal hub 12 to distal end 14. The lumen 22 is concentric to the central longitudinal axis 34 and is defined by a circular sidewall 36 which extends around central longitudinal axis 34.

As shown in FIGS. 2–4, the distal tip 24 is closed with a smoothing rounded dome portion 38. Extending through the dome portion 38 are a plurality of longitudinally extending holes or ports 40. Ports 40 as shown are 0.007 inches in diameter, however, the specific diameter shown is for illustrative purposes only. Obviously, the size of the ports can vary dependent on the total number of ports placed through the distal end.

In FIGS. 2–4, five (5) generally parallel longitudinally extending ports 40 are shown extending through distal tip 24. Such a phacoemulsification needle produces greater cavitation at its tip due partially to the existence of a greater amount of metal existing at the needle tip. Generally, such a needle is manufactured from titanium or stainless steel. A prior art phacoemulsification needle of the type shown in FIGS. 1a and 1b has a projected area of approximately 0.00037 square inches at its tip. This is determined by measuring the flat, radially extending material extending around the circumference of the needle tip. It is this surface that produces cavitation at the needle tip. In the phacoemulsification of the present invention, as shown in FIGS. 2 and 4, there exists a projected area approximately 0.00119 square inches of material which creates a greater amount of cavitation at its tip than the phacoemulsification needle of the prior art.

Figure 5:
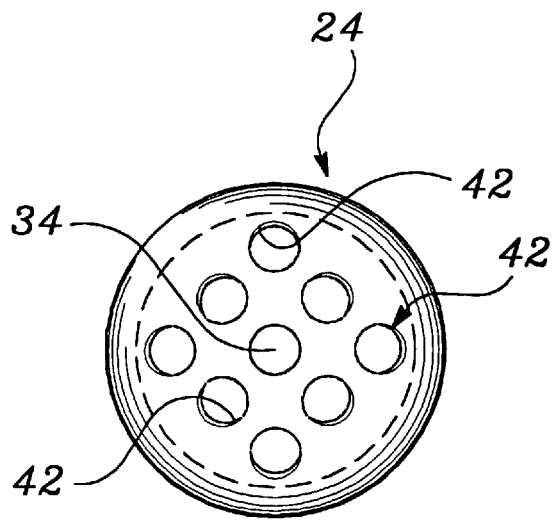
FIG. 5 is an enlarged distal end view of the phacoemulsification needle tip of a second embodiment of the present invention.

Referring now to FIG. 5, a second embodiment of the phacoemulsification needle of the present invention is shown. In FIG. 5, the distal tip 24 is shown having nine (9) generally parallel longitudinally extending ports 42. The phacoemulsification needle of FIG. 5 is provided with more material at the tip, thereby improving cavitation produced at the needle tip. In FIG. 5, the ports have a diameter of 0.005 inches by way of example.

The phacoemulsification needles of FIGS. 2 and 5 also help to decrease clogging of the needles. With standard phacoemulsification needles, the large size of the central opening allows larger pieces of the tissue to be aspirated into the central opening which can cause clogging either within the needle itself or in the aspiration conduit within the handpiece. However, a phacoemulsification needle of the present invention is provided with a plurality of smaller holes, only allowing smaller pieces of tissue to enter the needle, thereby preventing clogging of either the needle or aspiration conduit within the handpiece. And while it is known to provide such a phacoemulsification having a single smaller port such as in U.S. Pat. Nos. 4,825,865; 5,057,098; and, 5,112,239, these needles drastically effect fluid flow through the lumen of the needle. The present invention provides both increased cavitation as well as similar fluid flow characteristics to prior art needles to provide a non-clogging phacoemulsification needle with improved cavitation characteristics.

Whereas the present invention has been described with respect to specific embodiments thereof, it will be understood that various changes and modifications will be suggested to one skilled in the art and it is intended to encompass such changes and modifications as fall within the scope of the attached claims.

What is claimed:

1. In a phacoemulsification needle having a proximal end attachable to a phacoemulsification handpiece and a distal end for insertion into an eye; the needle having a central longitudinal axis extending from the proximal end to the distal end;
   a bore within the needle concentric to the central axis thereof, forming a lumen, the lumen having sidewalls therearound, including inner and outer surfaces with an opening at the proximal end of the needle, an improved distal tip comprising:
   a distal end having a smoothly rounded surface closed distal end;
   a plurality of ports positioned through the closed distal end communicating between the lumen and exteriorly to the needle;
   wherein there are five (5) ports extending through the closed distal end; and
   wherein the phacoemulsification needle is made of metal and the rounded surface closed distal end has approximally 0.00119 square inches of metal material at the distal tip to aid in the creation of cavitation at said tip.

2. In a phacoemulsification needle having a proximal end attachable to a phacoemulsification handpiece and a distal end for insertion into an eye; the needle having a central longitudinal axis extending from the proximal end to the distal end;
   a bore within the needle concentric to the central axis thereof, forming a lumen, the lumen having sidewalls therearound, including inner and outer surfaces with an opening at the proximal end of the needle, an improved distal tip comprising:
   a distal end having a smoothly rounded surface closed distal end;
   a plurality of ports positioned through the closed distal end communicating between the lumen and exteriorly to the needle;

wherein there are nine (9) ports extending through the closed distal end; and wherein the phacoemulsification needle is made of metal and the rounded surface closed distal end has approximately 0.00119 square inches of metal material at the distal tip to aid in the creation of cavitation at said tip.

3. In a phacoemulsification needle having a proximal end attachable to a phacoemulsification handpiece and a distal end for insertion into an eye; the needle having a central longitudinal axis extending from the proximal end to the distal end;

a bore within the needle concentric to the central axis thereof, forming a lumen, the lumen having sidewalls therearound, including inner and outer surfaces with an opening at the proximal end of the needle, an improved distal tip comprising:

a distal end having a smoothly rounded surface closed distal end;

a plurality of ports positioned through the closed distal end communicating between the lumen and exteriorly to the needle;

wherein there are five (5) ports extending through the closed distal end; and wherein the distal tip has ports with a diameter of approximately 0.007 inches to provide adequate fluid flow through said tip.

4. In a phacoemulsification needle having a proximal end attachable to a phacoemulsification handpiece and a distal end for insertion into an eye; the needle having a central longitudinal axis extending from the proximal end to the distal end;

a bore within the needle concentric to the central axis thereof, forming a lumen, the lumen having sidewalls therearound, including inner and outer surfaces with an opening at the proximal end of the needle, an improved distal tip comprising:

a distal end having a smoothly rounded surface closed distal end;

a plurality of ports positioned through the closed distal end communicating between the lumen and exteriorly to the needle;

wherein there are nine (9) ports extending through the closed distal end; and wherein the distal tip has ports with a diameter of approximately 0.005 inches to provide adequate fluid flow through said tip.

* * * * *